(12) United States Patent
Schultz

(10) Patent No.: US 7,981,164 B1
(45) Date of Patent: Jul. 19, 2011

(54) KNEE PROSTHESIS

(76) Inventor: Michael W. Schultz, Pillager, MN (US)

( * ) Notice: Subject to any disclaimer, the term of this patent is extended or adjusted under 35 U.S.C. 154(b) by 113 days.

(21) Appl. No.: 12/498,665

(22) Filed: Jul. 7, 2009

(51) Int. Cl.
*A61F 2/64* (2006.01)
*A61F 2/68* (2006.01)
(52) U.S. Cl. ........................................................ 623/44
(58) Field of Classification Search ............... 623/39–46
See application file for complete search history.

(56) References Cited

U.S. PATENT DOCUMENTS 5,181,931 A * 1/1993 van de Veen ................... 623/40
2009/0088867 A1* 4/2009 Andrysek ...................... 623/39
* cited by examiner

*Primary Examiner* — Bruce E Snow
(74) *Attorney, Agent, or Firm* — David A. Lingbeck

(57) ABSTRACT

A knee prosthesis for providing a user with a natural walking gait and flexion resistance. The knee prosthesis includes a support assembly; a flexion resistance member being supported upon the support assembly; a pivot assembly being pivotally connected to the support assembly and being fastened to a user's leg socket; and a flexion resistance drive assembly interconnecting said pivot assembly and said flexion resistance member.

13 Claims, 3 Drawing Sheets

KNEE PROSTHESIS

BACKGROUND OF THE INVENTION

1. Field of the Invention

The present invention relates to prosthetics and more particularly pertains to a new knee prosthesis for providing a user with a natural walking gait and flexion resistance.

2. Description of the Prior Art

The use of prosthetics is known in the prior art. More specifically, prosthetics heretofore devised and utilized are known to consist basically of familiar, expected and obvious structural configurations, notwithstanding the myriad of designs encompassed by the crowded prior art which have been developed for the fulfillment of countless objectives and requirements.

The prior includes a thigh frame, a leg frame, and an air cylinder interconnecting the thigh and leg frames with an adjusting means for the air cylinder and also includes a phase detector for detecting swing phases and stance phases, walking speed detector for detecting an actual walking speed, and control unit for adjusting the degree of opening of the valve of the air cylinder corresponding to the actual walking speed. Another prior art includes a leg frame and also includes an actuator motor/generator to control gait and/or to generate electrical energy, and also includes an air cylinder being pivotally connected to a lever which is coupled to a knee assembly. While these devices fulfill their respective, particular objectives and requirements, the aforementioned patents do not disclose a new knee prosthesis.

SUMMARY OF THE INVENTION

The general purpose of the present invention, which will be described subsequently in greater detail, is to provide a new knee prosthesis which has many of the advantages of the prosthetics mentioned heretofore and many novel features that result in a new knee prosthesis which is not anticipated, rendered obvious, suggested, or even implied by any of the prior art prosthetics, either alone or in any combination thereof. The present invention includes a support assembly; a flexion resistance member being supported upon the support assembly; a pivot assembly being pivotally connected to the support assembly and being fastened to a user's leg socket; and a flexion resistance drive assembly interconnecting said pivot assembly and said flexion resistance member. None of the prior art includes the combination of the elements of the present invention.

There has thus been outlined, rather broadly, the more important features of the knee prosthesis in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new knee prosthesis which has many of the advantages of the prosthetics mentioned heretofore and many novel features that result in a new knee prosthesis which is not anticipated, rendered obvious, suggested, or even implied by any of the prior art prosthetics, either alone or in any combination thereof.

Still another object of the present invention is to provide a new knee prosthesis for providing a user with a natural walking gait and flexion resistance.

Still yet another object of the present invention is to provide a new knee prosthesis that provides more flexion angle and more controlled resistance.

Even still another object of the present invention is to provide a new knee prosthesis that uses adjustable compressed gas to assist in the user's stance ranging from a full squat to standing upright.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
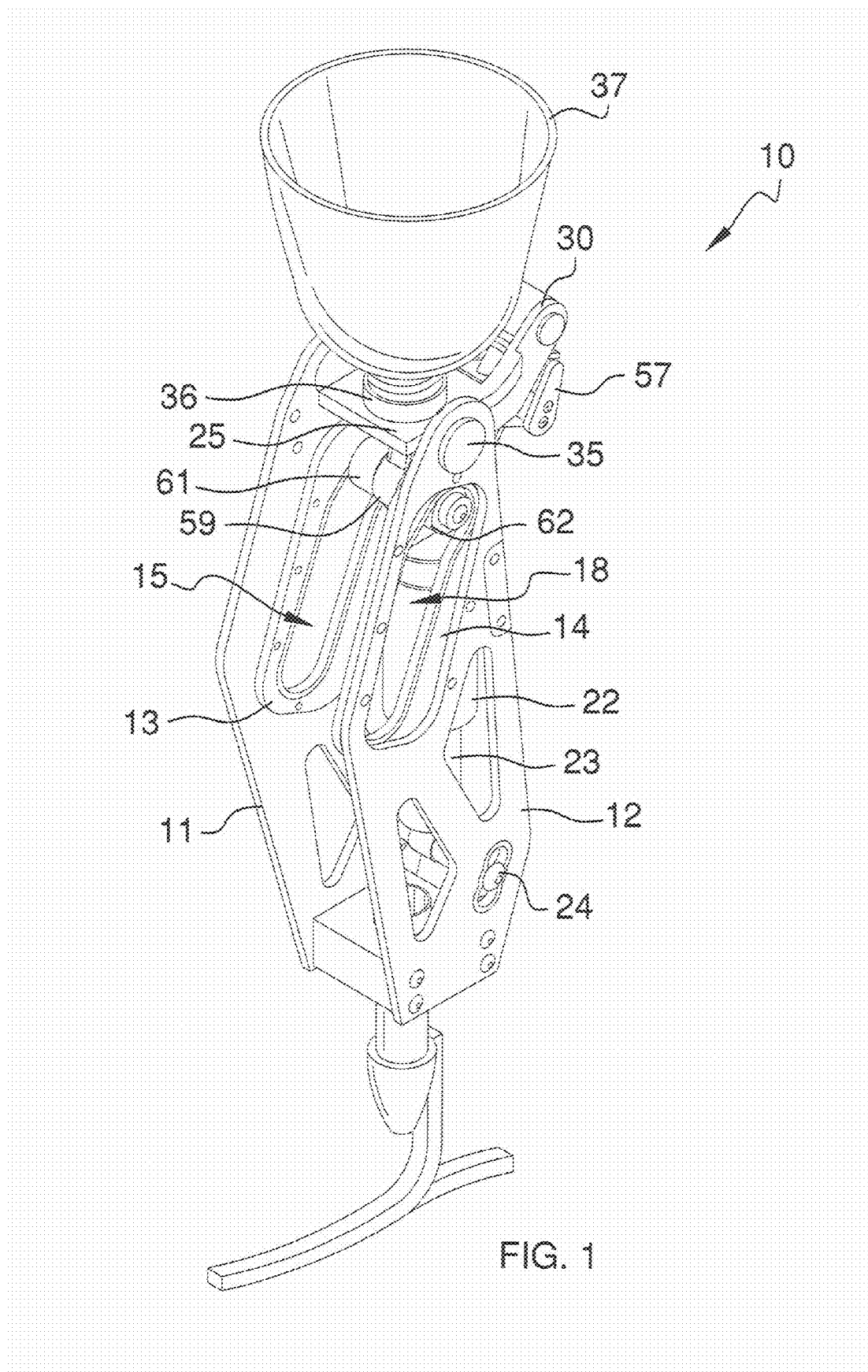
FIG. 1 is an upper front perspective view of a new knee prosthesis according to the present invention.
Figure 2:
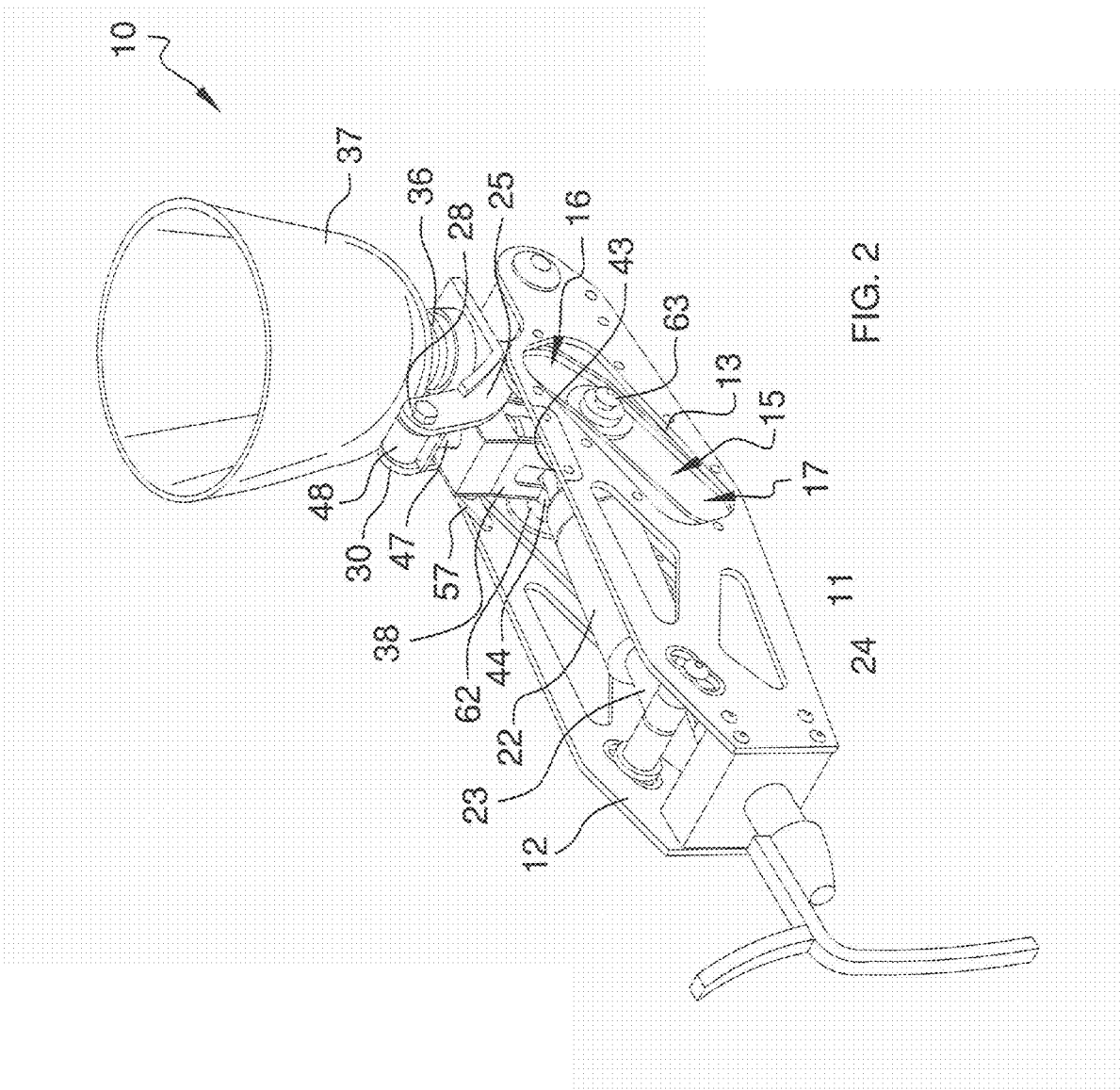
FIG. 2 is a lower rear perspective view of the present invention.
Figure 3:
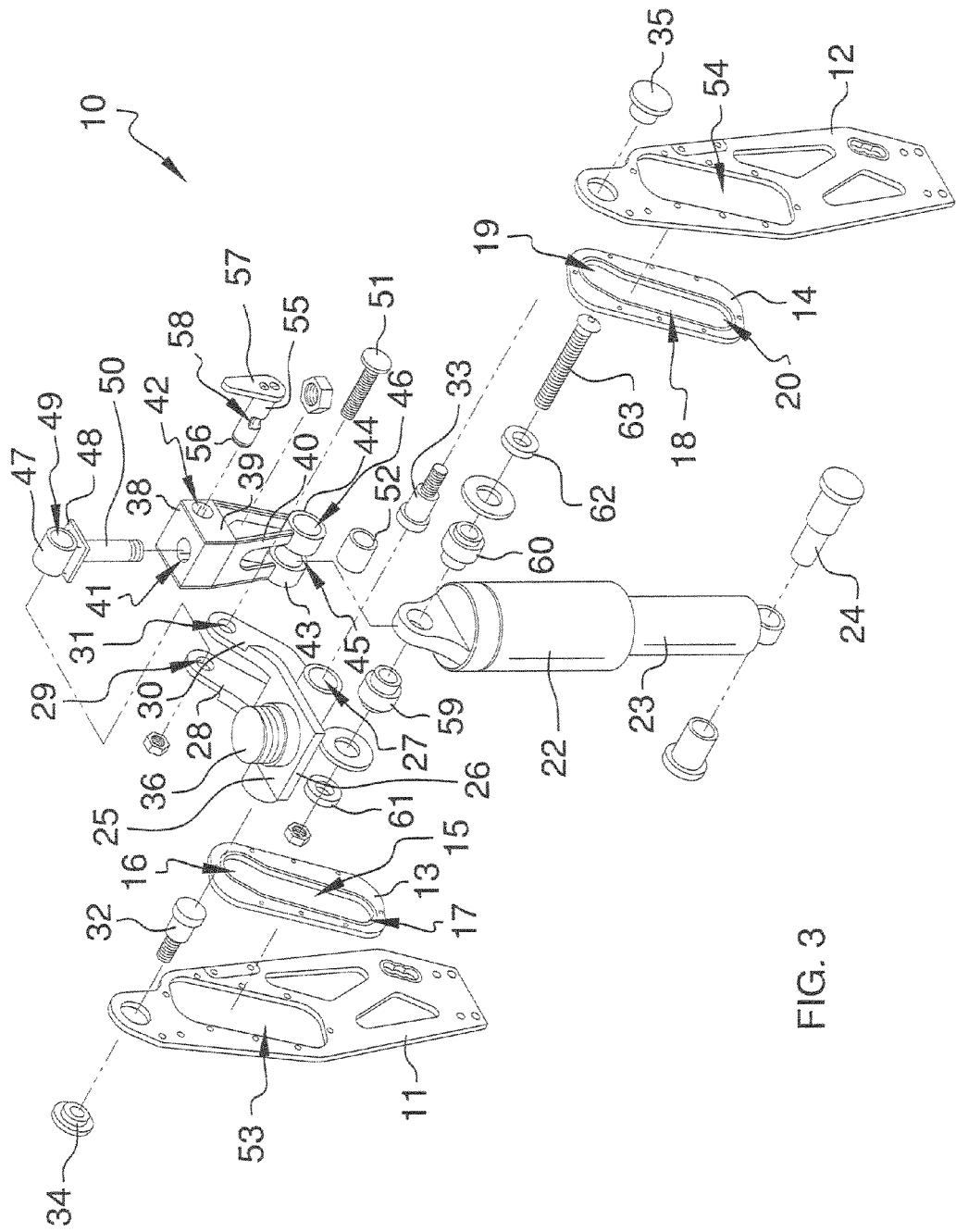
FIG. 3 is an exploded perspective view of the present invention.

With reference now to the drawings, and in particular to FIGS. 1 through 3 thereof, a new knee prosthesis embodying the principles and concepts of the present invention and generally designated by the reference numeral 10 will be described.

As best illustrated in FIGS. 1 through 3, the knee prosthesis 10 generally comprises a support assembly and includes a pair of plate members 11,12 being spacedly arranged and disposed generally parallel to one another with the plate members 11,12 being conventionally interconnected. Each of the plate members 11,12 includes an elongate roller guide slot 15,18. Each elongate roller guide slot 15,18 is disposed through a respective plate member 11,12 with each elongate roller guide slot 15,18 extending longitudinally, forwardly and downwardly from near a top of a respective plate member 11,12. Each elongate roller guide slot 15,18 has an upper portion 16,19 which is angled relative to the coronal plane and also has a lower portion 17,20 which is angled relative to a coronal plane and to the upper portion 16,19. The upper portion 16,19 of each elongate roller guide slot 15,18 is disposed at a greater angle than that of the lower portion 16,19 relative to the coronal plane to reduce flexion resistance during a user's normal gait and at a beginning of any degree of flexion.

As a second embodiment, each plate member 11,12 has an opening 53,54 being disposed therethrough. The support assembly also includes interchangeable plate inserts 13,14 being removably and individually fastened with fasteners in each opening 53,54 of a respective plate member 11,12. Each elongate roller guide slot 15,18 is disposed through a respective plate insert 13,14 with each elongate roller guide slot 15,18 extending longitudinally, forwardly and downwardly of a respective plate insert 13,14. Each elongate roller guide slot 15,18 has an upper portion 16,19 which is angled relative to the coronal plane and also has a lower portion 17,20 which is angled relative to the coronal plane and to the upper portion 16,19. The upper portion 16,19 of each elongate roller guide slot 15,18 is disposed at a greater angle than that of the lower portion 17,20 relative to the coronal plane to reduce flexion resistance during a user's normal gait and at a beginning of any degree of flexion. The elongate roller guide slots 15,18 are distinctively angled for each pair of interchangeable plate inserts 13,14 to allow a user to select a particular flexion resistance.

A flexion resistance member 23,23 is conventionally supported upon the support assembly. The flexion resistance member 22,23 is adjustable and includes a cylinder 22 with compressed gas being disposed therein and also includes a piston 23 being movably and conventionally disposed relative to the cylinder 22 for providing adjustable flexion resistance while moving or in a stationary position. The piston 23 is conventionally fastened at a bottom end thereof with fasteners to the plate members 11,12 with the cylinder 22 and the piston 23 being disposed between the plate members 11,12.

A pivot assembly is pivotally connected to the support assembly and is fastened to a user's leg socket 37. The pivot assembly includes a pivot member 25 having a main portion 26 and having finger-like projections 28,30 integrally extending from the main portion 26. The main portion 26 has a bore 27 extending transversely therethrough near a first end of the main portion 26. The pivot assembly also includes a leg socket connector 36 being conventionally attached to the pivot member 25, and further includes connectors including bolts 32,33 and flanged bearings 34,35 being disposed in or through the bore 29 of the main portion 26 and through the plate members 11,12 to pivotally connect the pivot member 25 to the plate members 11,12.

A flexion resistance drive assembly interconnects the pivot assembly and the flexion resistance member 22,23. The flexion resistance drive assembly includes a first linkage member 38 being pivotally connected to the flexion resistance member 22,23, and also includes a second linkage member 47 being engageable to the first linkage member 38 and being pivotally connected to the finger-like projections 28,30 of the pivot member 25. The first linkage member 38 has a first bore 41 extending longitudinally therethrough and has an upper portion 39 and a lower portion 40. The upper portion 39 has a second bore 42 extending transversely therethrough. The lower portion 40 has finger-like projections 43,44 extending downwardly integrally therefrom and having third and fourth bores 45,46 extending transversely therethrough. The second linkage member 47 is movably and engageably disposed in the first bore 41 of the first linkage member 38. The second linkage member 47 includes a head portion 48 and a shaft portion 49 which is longitudinally movable in the first bore 41. The head portion 48 has a bore 49 being transversely disposed therethrough with a bushing 52 being conventionally disposed therein and a bolt being disposed through the bushing 52 and bore 49 and through the holes 29,31 of the finger-like projections 28,30 of the pivot member 25 to pivotally connect the second linkage member 47 to the pivot member 25. The head portion 49 has a dimension larger than that of the first bore 41 of the first linkage member 38 to engage the first linkage member 38 and to activate the flexion resistance member 22,23 at a desired degree of flexion. The flexion resistance drive assembly further includes a key member 55 being positionably disposed in the second bore 42 of the first linkage member 38 and is engageable to the second linkage member 47 to engage and disengage the first and second linkage members 38,47 and to activate and deactivate the flexion resistance member 22,23 at various desired degrees of flexion. The key member 55 includes a shaft 56 and a handle 57 being conventionally connected to the shaft 56 with the shaft 56 being rotatably disposed in the second bore 42 to either engage the second linkage member 47 and activate the flexion resistance member 22,23 at a desired degree of flexion or disengage the second linkage member 47 and deactivate the flexion resistance member 2,23 to allow uninhibited motion of the knee prosthesis 10 relative to the leg socket 37 until the head portion 48 of the second linkage member 47 engages the first linkage member 38 which then activates the flexion resistance member 22,23. The shaft 56 of the key member 55 has a slot 58 being disposed in a side thereof with the slot 58 being dimensioned to allow the shaft portion 50 of the second linkage member 47 to move uninhibited in the first bore 41 and in the slot 58 of the key member 55. The slot 58 of the key member 55 is rotatable away from the second linkage member 47 for the key member 55 to engage the second linkage member 47 to the first linkage member 38 to activate the flexion resistance member 22,23 at a desired degree of flexion. The flexion resistance drive assembly also includes a roller member 59-63 having bushings 59,58, bearings 61,62 and a bolt 63 interconnecting the first linkage member 38 at a top end of the flexion resistance member 22,23 and being disposed through the third and fourth bores 45,46 of the first linkage member 38 and having ends each being movably disposed in a respective elongate roller guide slot 15,18 to control the amount of resistance exerted by the flexion resistance member 22,23.

In use, the user fits the leg socket 37 about one's leg and stands on the knee prosthesis 10. The upper portions 16,17 of the elongate roller guide slots 15,18 reduce the amount of resistance exerted by the flexion resistance member 22,23 at the beginning of any degree of flexion which allows the user to more easily swing one's knee prosthesis 10 during a normal gait. If the user squats, the ends of the roller member 59-63 moves from the upper portions 16,19 to the lower portions 17,20 of the elongate roller guide slots 15,18; whereupon, the flexion resistance member 22,23 exerts more flexion resistance and aids the user to stand upright after squatting. In addition, the user can freely swing one's knee prosthesis 10 with no resistance during a normal gait and no squatting by rotating the key member 55 to disengage the second linkage member 47 from the first linkage member 38 with the second linkage member 47 only engaging the first linkage member 38 after a desired degrees of flexion. The second linkage member 47 moves freely relative to the first linkage member 38 without activating the flexion resistance member 22,23. If the user desires to have at least minimal flexion resistance at the beginning of any degree of flexion, the user then rotates the key member 55 to engage the first and second linkage members 38,47 which activates the flexion resistance member 22,23.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the knee prosthesis. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A knee prosthesis comprising:
 a support assembly including a pair of plate members being spacedly arranged and disposed generally parallel to one another, each of said plate members including an elongate roller guide slot, each said elongate roller guide slot being disposed through a respective said plate member, each said elongate roller guide slot having an upper portion which is angled relative to a longitudinal axis of a respective said plate member and also having a lower portion which is angled relative to the longitudinal axis of a respective said plate member, said upper portion of each said elongate roller guide slot being disposed at a greater angle than that of said lower portion relative to the longitudinal axis of a respective said plate member to reduce flexion resistance during a user's normal gait and at a beginning of any degree of flexion;
 a flexion resistance member being supported upon said support assembly;
 a pivot assembly being pivotally connected to said support assembly and being fastened to a user's leg socket; and
 a flexion resistance drive assembly interconnecting said pivot assembly and said flexion resistance member.

2. The knee prosthesis as described in claim 1, wherein said flexion resistance member includes a cylinder with compressed gas being disposed therein and also includes a piston being movably disposed relative to said cylinder for providing adjustable flexion resistance while moving or in a stationary position.

3. A knee prosthesis comprising:
 a support assembly including a pair of plate members being spacedly arranged, each of said plate members including an elongate roller guide slot, each said plate member having an opening being disposed therethrough, said support assembly having interchangeable plate inserts being removably and individually fastened in each said opening of a respective said plate member;
 a flexion resistance member being supported upon said support assembly;
 a pivot assembly being pivotally connected to said support assembly and being fastened to a user's leg socket; and
 a flexion resistance drive assembly interconnecting said pivot assembly and said flexion resistance member.

4. The knee prosthesis as described in claim 3, wherein each said elongate roller guide slot is disposed through a respective said plate insert, each said elongate roller guide slot extending longitudinally, forwardly and downwardly of a respective said plate insert.

5. The knee prosthesis as described in claim 4, wherein each said elongate roller guide slot having an upper portion which is angled relative to a longitudinal axis of a respective said plate insert and also having a lower portion which is angled relative to the longitudinal axis of a respective said plate insert and also to said upper portion.

6. The knee prosthesis as described in claim 5, wherein said upper portion of each said elongate roller guide slot is disposed at a greater angle than that of said lower portion relative to the longitudinal axis of a respective said plate insert to reduce flexion resistance during a user's normal gait and at a beginning of any degree of flexion, said elongate roller guide slots being distinctively angled for each pair of said interchangeable plate inserts to allow a user to select a particular flexion resistance.

7. A knee prosthesis comprising:
 a support assembly including a pair of plate members being spacedly arranged;
 a flexion resistance member being supported upon said support assembly;
 a pivot assembly being pivotally connected to said support assembly and being fastened to a user's leg socket, said pivot assembly including a pivot member having a main portion; and
 a flexion resistance drive assembly interconnecting said pivot assembly and said flexion resistance member, said flexion resistance drive assembly including a first linkage member being pivotally connected to said flexion resistance member, and also including a second linkage member being engageable and movable relative to said first linkage member and being pivotally connected to said pivot member to activate said flexion resistance member at desired degrees of flexion.

8. The knee prosthesis as described in claim 7, wherein said first linkage member has a first bore extending longitudinally therethrough and has an upper portion and a lower portion, said upper portion having a second bore extending transversely therethrough, said lower portion having at least one finger-like projection extending downwardly therefrom and having at least one bore extending transversely therethrough, said second linkage member being movably and engageably disposed in said first bore of said first linkage member.

9. The knee prosthesis as described in claim 8, wherein said second linkage member includes a head portion and a shaft portion which is longitudinally movable in said first bore, said head portion having a bore being transversely disposed therethrough and having a dimension larger than that of said first bore of said first linkage member to engage said first linkage member and to activate said flexion resistance member at a desired degree of flexion, said second linkage member being pivotally connected to said pivot member.

10. The knee prosthesis as described in claim 8, wherein said flexion resistance drive assembly further includes a key member being positionably disposed in said second bore of said first linkage member and being engageable to said second linkage member to engage and disengage said first and second linkage member and to activate and deactivate said flexion resistance member at various desired degrees of flexion.

11. The knee prosthesis as described in claim 10, wherein said key member includes a shaft and a handle being connected to said shaft, said shaft being rotatably disposed in said second bore to either engage said second linkage member and activate said flexion resistance member at a desired degree of flexion or disengage said second linkage member and deactivate said flexion resistance member to allow uninhibited motion of the knee prosthesis relative to the leg socket until said head portion of said second linkage member engages said first linkage member which then activates said flexion resistance member.

12. The knee prosthesis as described in claim 11, wherein said shaft of said key member has a slot being disposed in a side thereof, said slot being dimensioned to allow said shaft portion of said second linkage member to move uninhibited in said first bore and in said slot of said key member, said slot of said key member being movable away from said second linkage member with said key member engaging said second linkage member to said first linkage member.

13. The knee prosthesis as described in claim 7, wherein said flexion resistance drive assembly also includes a roller member interconnecting said first linkage member to said flexion resistance member and having ends each being movably disposed in a respective said elongate roller guide slot to control the amount of resistance exerted by said flexion resistance member.

* * * * *